United States Patent [19]
Hoerrmann

[11] Patent Number: 6,153,643
[45] Date of Patent: Nov. 28, 2000

[54] ANTI-CANCER-SUBSTANCE

[76] Inventor: Wilhelm Hoerrmann, Staltacher Str. 34, D-82393 Iffeldorf, Germany

[21] Appl. No.: 09/336,481

[22] Filed: Jun. 18, 1999

Related U.S. Application Data

[63] Continuation-in-part of application No. 09/119,312, Jul. 20, 1998, abandoned, which is a continuation-in-part of application No. 08/859,341, May 20, 1997, abandoned, which is a continuation-in-part of application No. 07/223,774, Dec. 29, 1986, abandoned, which is a continuation-in-part of application No. 06/668,200, Nov. 5, 1984, abandoned.

[51] Int. Cl.$^7$ ..................................................... A61K 31/40
[52] U.S. Cl. ................................................................ 514/423
[58] Field of Search ............................................. 514/423

[56] References Cited

PUBLICATIONS

Strum et al., Lab. Invest., 4b(4), 347–354, 1981.
Dyer, NIH, PP 10–12, 143 and 144, 1949.

*Primary Examiner*—Jerome D. Goldberg

[57] ABSTRACT

This application refers to the use of cis-4-hydroxy-L-proline for the treatment of cancer.

2 Claims, No Drawings

ANTI-CANCER-SUBSTANCE

This Application is a Continuation in Part Application of Ser. No. 09/119,312 Jul. 20, 1998 abandoned which is a Continuation in Part Application of Ser. No. 08/859,341 filed May 20, 1997 abandoned which is a Continuation in Part Application of Ser. No. 07/223,774 filed Dec. 29, 1986 abandoned which is a Continuation in Part Application of Ser. No. 06/668,200 filed Nov. 5, 1984 abandoned. The enclosed terminal disclaimer is to be recorded on this continuing application.

This application refers to the use of a special isomer of hydroxyproline namely cis-4-hydroxy-L-proline for the treatment of cancer. The invention is directed first of all, but not limited to, to the treatment of the subgroup of cancer consisting of carcinomas and tumors of neuroectodermal origin as there are gliomas and melanomas.

As contrasted with conventional chemotherapy, which is highly toxic and in many cases ineffective, the compound of the invention is free of bad side effects and yet effective.

Considering the prior art of Helen M. Dyer (An Index of Tumor Chemotherapy, INH 10–12, 143–144, 1949) three facts are to be mentioned: 1. In Dyer's work "No attempt has been made to use a consistent system of nomenclature for the chemical agents". That means that the exact chemical nature of the agents examined by Dyer is actually unknown, 2. Dyer observed anti-tumor-effects only with sarcomas, not with carcinomas. As contrary to carcinomas sarcomas are possibly influenced already by unspecific stimuli it is to be doubted that there were genuine anti-tumor-effects at all. 3. Dyer made her examinations in the years 1933–45 with methods which are for very good reason not longer used in oncology. The reason is that such results are not transferable and not predicting to cases of human cancer.

Applicant founded his research work on cell cultures of cancer cells of human origin (removed by surgeon from cancer patient) at a time where that was not general custom. And his results in preclinical tests clearly showed the high anti-cancer activity of the compound in form of antprolifertive, redifferentiating, cell and cell nucleus stabilizing and agglutination normalizing effects. This new and unexpected results were published by applicant:

Biol.Chem.Hoppe-Seyler P 869, Vol 366 (1985)

Biol.Chem.Hoppe-Seyler P 375, Vol 367 (1986)Suppl.

Canc.Detect.a.Prevent. Vol 11, No 1/2 (1987), 2:046

Later cis-4-hydroxy-L-proline were administered by hospital physicians to patients suffering from severe and progressive colorectal adenocarcinoma.

There was in all cases a considerable relief or even a complete disappearence of pain caused by livermetastasis or local recidives in the pelvis or both. It is quite apparently that this relief of pain was not due to an (non existing) analgetic effect of the compound, but to a reduction of invasive tumor pressure. This was accompanied by a considerable improvement in the general condition and fitness of the patients in most cases. The clinical evidence available at present is from the statistical standpoint of view not sufficient to proof that a prolongation of the lifespan of the patients could be achieved by this treament, though this is probable. It can be said however that nearly always the progression of the disease was delayed or even stopped. All this improvements in the patients state could be achieved without side effects. No pathological laboratory findings or nausea or vomiting or loss of hair had to be attributed to the treatment. That is even true in cases who had administered cis-4-hydroxy-L-proline uninterrupted daily for one full year. The dosis of 4 g pro die given orally was able to improve the liver condition, but for the treatment of local recidives intravenously administering 6 g pro die was necessary.

This good clinical results observed in cases of colorectal adenocarcinoma induced applicant to investigate whether or not cancer in other organs and of other kind could also be treated with the compound. This made it necessary to return again to preclinical research but this time not with general oncologic aspects as described above in mind, but to investigate in cell cultures of human origin special manifestations of cancer. This research is as yet not completed, nevertheless interesting details can already be stated. It was from priviouly obtained experiences to expect that brain tumors would react. But it was really surprisingly that even the cancer cells of the brain tumor with the highest malignity, namely the glioblastoma multiforme, shows a very pronounced reduction of cancer cell proliferation. Interestingly too the results with cancer cells of prostate cancer. The hormone= andropene sensitive variety of this cancer (appr. 80% of the clinical cases) reacted promptly, while the non-hormone sensitive cells did not. This differential reaction of two varieties of carcinomas in the same gland clearly demonstrate the high specifity of the compound used.

cis-4-hydroxy-L-proline is a non toxic compound with an acute toxicity higher than 10000 mg/kg and therefore a wide dosis range may be administered. However 0.05–0.20 g/kg daily will be sufficient in most cases. The general known contraindications of amino acid therapy should however be taken into account, especially in cases of renal failures. The administering is preferably orally or intravenously or eventually locally whereby the general methods of pharmaceutics are to be applied.

The compound may also be administered in the form of pharmaceutically acceptable derivatives or precursors for example salts, acid addition salts, ester, amide, acid amide, ether, dehydroproline and the corresponding keto compound, chemical modifications which are in itself all known to the art.

What is claimed is:

1. A method of treating carcinoma sensitive to cis-4-hydroxy-L-proline administering to such a carcinoma-patient in an effective daily amount 0.05–0.20 g/kg of cis-4-hydroxy-L-proline.

2. A method according to claim 1 whereby the patient is suffering from cis-4-hydroxy-L-proline sensitive carcinoma of prostate, brain or colorectum.

* * * * *